(12) United States Patent
Kureshy et al.

(10) Patent No.: US 7,666,819 B2
(45) Date of Patent: *Feb. 23, 2010

(54) INTEGRATED MICRO ARRAY SYSTEM AND METHODS THEREFOR

(75) Inventors: Fareed Kureshy, Del Mar, CA (US); Vijay K. Mahant, Murrieta, CA (US); Shailendra Singh, Carlsbad, CA (US)

(73) Assignee: Autogenomics, Inc.

( * ) Notice: Subject to any disclaimer, the term of this patent is extended or adjusted under 35 U.S.C. 154(b) by 422 days.

This patent is subject to a terminal disclaimer.

(21) Appl. No.: 10/513,485

(22) PCT Filed: May 29, 2002

(86) PCT No.: PCT/US02/17006

§ 371 (c)(1),
(2), (4) Date: Nov. 2, 2004

(87) PCT Pub. No.: WO03/102241

PCT Pub. Date: Dec. 11, 2003

(65) Prior Publication Data

US 2005/0233325 A1 Oct. 20, 2005

(51) Int. Cl.
*C40B 50/00* (2006.01)

(52) U.S. Cl. .................. 506/23; 435/6; 435/7.1; 435/7.2

(58) Field of Classification Search .......... None
See application file for complete search history.

(56) References Cited

U.S. PATENT DOCUMENTS

| | | | |
|---|---|---|---|
| 4,623,008 A * | 11/1986 | Shibata et al. ............. 141/89 |
| 5,366,896 A | 11/1994 | Margrey et al. | |
| 5,632,957 A | 5/1997 | Heller et al. | |
| 6,159,681 A * | 12/2000 | Zebala .................... 435/4 |
| 6,187,267 B1 * | 2/2001 | Taylor et al. ............ 422/52 |
| 6,471,916 B1 * | 10/2002 | Noblett .............. 422/82.08 |
| 6,838,051 B2 * | 1/2005 | Marquiss et al. ......... 422/63 |
| 7,354,389 B2 * | 4/2008 | Kureshy et al. .......... 506/37 |
| 2002/0018991 A1 | 2/2002 | Rava et al. | |

FOREIGN PATENT DOCUMENTS

| | | |
|---|---|---|
| DE | 4312093 | 10/1993 |
| EP | 1126272 | 8/2001 |
| EP | 1132458 | 9/2001 |
| WO | WO 95/11454 | 4/1995 |
| WO | WO 01/84434 | 11/2001 |

OTHER PUBLICATIONS

Schena M., et al., "Parallel Human Genome Analysis: Micorarray-Based Expressiong Monitoring of 1000 Genes," Proceedings of the National Academy of Sciences of USA, vol. 93, No. 20, Oct. 1996, pp. 10614-10679, Washington, US.

* cited by examiner

Primary Examiner—Jeffrey S. Lundgren
(74) Attorney, Agent, or Firm—Fish & Richardson, PC (57) ABSTRACT

Various methods are provided for an integrated micro array system (100) that allows fully automated sample processing and detection/quantification of nucleic acid and protein samples in a single analytical device, which may be configured to communicate data to a person other than the person operating the device. The integrated micro array system has a housing (110) in which robotics assembly (120) controls motion of automatic pipette (124) and second actuator (122) that control motion of the automatic actuator (123). Fluidics station (130) includes a plurality of multi-reagent packs (132). Sample station (140) comprises a plurality of sample vessels (142). Pipette tip storage area (150) and magazine holder (160) that includes a plurality of magazine (162). The system also comprise of a sample processing platform (170), a stringency station (181), and optical detector (180), and a data transfer device (190).

21 Claims, 6 Drawing Sheets

INTEGRATED MICRO ARRAY SYSTEM AND METHODS THEREFOR

FIELD OF THE INVENTION

The field of the invention is micro array systems, and particularly automated micro array systems.

BACKGROUND OF THE INVENTION

Recent advances in genomics and proteomics research made numerous nucleotide and peptide sequences available, necessitating high-throughput screening of samples for presence and/or quantity of genes and/or gene expression. While automation of individual steps (e.g., DNA isolation, protein fractionation, etc.) in high-throughput screening may be performed using relatively simple instrument configurations, integration of multiple and distinct steps in automated high-throughput screening remains problematic.

For example, sample analysis for detection and quantification of one or more analytes may be performed in nano-volumes on a single chip (see e.g., "Lab-on-a-chip" from Agilent or Caliper Technologies). Such multiple analyte detection can advantageously be performed in relatively short time using minimal amounts of sample. Moreover, all steps from handling of the sample after application of the sample to detection and analysis are performed within the same device. However, identification and quantification of the detected analyte using nanoelectrophoresis is typically restricted to the size of the analyte. Moreover, resolution of individual analytes becomes increasingly difficult as the size or charge difference between the analytes decreases. Consequently, such nanoelectrophoretic systems are generally limited to characterization of an analyte by its molecular weight.

Where high resolution of molecular weights of an analyte is particularly important, analysis of complex samples may be coupled with laser desorption—time of flight mass spectroscopic analysis (see e.g., Ciphergen Biosystems' LD-TOF multi-analyte desorption chips, or Sequenome chip). Here, components of a complex sample are immobilized on a carrier chip (e.g., chip with anion exchange resin or hydrophobic interaction resin) and subjected to size analysis after desorption according to their molecular properties in an analysis system. LD-TOF coupled analysis is typically highly sensitive and often requires only minimal sample preparation. Moreover, LD-TOF coupled analysis provides relatively high resolution among particular analytes. However, identification of particular analytes is still mostly limited to size determination.

Alternatively, and especially where the analyte is a DNA or RNA, various formats of automated modular PCR-based analysis are known in the art. For example, where a single sample is analyzed for presence or absence of a particular sequence, all or almost all of the reagents and sample may be introduced into an automated system from a single cartridge (see e.g., Cepheid's i-CORE system). On the other band, and especially where a relatively high number of samples are concurrently analyzed, a full robotic PCR station may be employed (see e.g., Orchid Biocomputer SNP Analysis system). Such systems typically provide an analysis procedure that integrates sample manipulation with nucleic acid amplification and product analysis. However, automated modular PCR-based analysis typically rely on amplification of target DNA to generate appreciable signals, thereby introducing significant complexity and numerous error-prone procedures. Moreover, while PCR based systems are frequently operated in a dedicated environment using dedicated equipment to prevent non-sample specific signals, problems associated with contamination via sample carry-over may still persist. Thus, automated modular PCR-based analysis tends to be highly expensive, and is generally limited to exclusive analysis of nucleic acids.

In still further examples, nucleic acid-containing samples can be analyzed by their hybridization characteristics with at least partially complementary and immobilized nucleic acids, thereby providing quantitative and qualitative information on a particular sample. Hybridization of a nucleic acid to corresponding solid-phase immobilized nucleic acids may be controlled by variation of temperature and/or ionic strength of the environment of the nucleic acid hybrid, and there are numerous systems known in the art.

For example, high density arrays of immobilized oligonucleotides on a silicon chip may be exposed to a sample containing nucleic acids that are complementary to at least some of the immobilized oligonucleotides (see e.g., Affymetrix' GeneChip system). In such systems, a processed sample (typically a labeled and biotinylated in-vitro transcript of a previously prepared cDNA) is provided to the chip in a fluidics station that further controls flow of reagents and hybridization temperature. After complementary labeled nucleic acids have hybridized to the corresponding nucleic acids on the chip, the chip is removed from the fluidics station and manually transferred to a scanner station in which the sample is analyzed via detection of the fluorescent labels. While such analytic devices typically allow a user to determine identity, presence, and/or quantity of a vast number of DNA/RNA analytes in a sample, substantial sample preparation (typically several hours to more than one day) and hybridization times (e.g., about 16 hours at 40° C.) are frequently necessary. Moreover, analytes detected and quantified using such systems tend to be limited to nucleic acids.

Alternatively, sample capture and hybridization may be controlled via electrostatic forces (see e.g., Nanogen's Nano-Chip system). In such systems, capture probes and hybridization conditions may be individually controlled, thereby allowing custom addressing of individual analyte pixels. However, due to the complexity of loading and reading procedures, the analytic process is split among at least two independent devices: Analytes are typically bound in a loader section, while a reader (i.e., array processor and scanner) will perform the readout of the sample.

In another system, detection may be performed using an electronic chip that provides a signal upon binding of a signaling oligonucleotide to an analyte oligonucleotide that is bound to a corresponding oligonucleotide that is immobilized on the chip (see e.g., Motorola's iSensor system). While electronic detection and quantification may provide at least some advantages, most of such systems are prone to non-specific false-positive and/or false-negative signals due to contamination. Moreover, analytes detected and quantified using such systems tend to be limited to nucleic acids.

Thus, although various systems for micro array systems are known in the art, numerous problems still remain. Among other things, while various systems may provide at least some automation, fluid handling and sample detection/quantification of analyte binding are typically operated in separate devices, thus requiring at least some user intervention after the sample is applied to the system. Furthermore, all or almost all of the known micro array systems are limited to analysis of either nucleic acids or peptides. Therefore, there is still a need for an improved methods and systems for automated analytic devices.

SUMMARY OF THE INVENTION

The present invention is directed to methods of operating analytical devices, and especially to methods of operating automated micro array systems that allow fully automated sample processing and detection/quantification of various analytes (e.g., nucleic acid, protein samples, low molecular weight compounds, etc.) in a single analytical device.

In one aspect of the inventive subject matter, a method of analyzing an analyte on a biochip has one step in which an analytical device is provided that includes a first section and a second section that receive a biochip having a plurality of substrates in a plurality of predetermined positions. In another step, the biochip is contacted in the first section with a sample containing a non-analyte and an analyte under conditions that allow binding of the analyte to at least one of the substrates, and in a still another step, the first section is operationally to the second section such that the biochip is automatically transferred from the first section to the second section. In a further step, binding of the analyte to the at least one of the substrates on the biochip is optically detected in the second section.

Contemplated biochips may be provided to the first section from a magazine using an automatic actuator, wherein the magazine is disposed within the analytical device, and it is further preferred that the first section may be configured to receive at least a second biochip. The first section may additionally include an energy source (e.g., ultrasound, microwave, and/or heat/cool source). Contemplated samples may include biological fluids with tissue, nucleic acids, peptides, and/or enzyme inhibitor as analytes. Consequently, suitable substrates include nucleic acids, peptides, and/or enzymes, which may or may not be non-covalently coupled to the biochip via a crosslinker.

Preferred steps of contacting may include pipetting the sample with an automatic pipette that is disposed within the analytical device, wherein the biochip may or may not be heated. Especially contemplated steps of operationally coupling include providing an automatic actuator that moves the biochip from a first platform of the first section to a second platform of a second section, while preferred steps of optically detecting include detection of a fluorescence signal, a chemiluminescence signal, and/or a phosphorescence signal with a confocal microscope or a dark field microscope, which may be focused using a reference signal from a reference marker that is disposed on the biochip.

In another aspect of the inventive subject matter, a method of analyzing an analyte on a biochip may include one step in which a biochip with a reference marker and a plurality of substrates is provided, wherein at least one of the substrates binds an analyte. In another step, the reference marker (e.g., comprising a fluorophor, luminogenic substrate, and/or a phosphorescent compound) is illuminated to create a reference signal, and the analyte is illuminated to create an analyte signal. In yet another step, a focal plane is determined for an optical detector using the reference signal and adjusting the optical detector to the focal plane, and in a further step, the analyte signal is acquired using the optical detector.

Preferred illumination of the reference marker and/or the analyte includes dark filed illumination, and illumination of the analyte with a laser is particularly preferred. Further especially contemplated illuminations for the reference marker and the analyte may be performed using independent light sources.

In a further aspect of the inventive subject matter, a method of operating an analytical includes one step in which an analytical device is provided comprising a data transfer interface coupled to a detector, a multi-reagent pack, an automatic pipette, and/or a sample processing platform. In another step, the data transfer interface is electronically coupled with a person other than a user of the analytical device, and in still another step, data are provided from the detector, the multi-reagent pack, the automatic pipette, and/or the sample processing platform to the person via the data transfer interface. In a further step, the data are employed to analyze operational status of the analytical device.

Particularly preferred methods of operation include those in which the person other than the user is in a remote location relative to the analytical device, and in which the step of providing is executed via an Internet or via a modem connection. Data may be provided in response to an action of the user of the analytical device, or in response to a request by the person other than the user. Contemplated data may relate to the batch number, date manufactured, expiration date, or type of reagent in the multi-reagent pack, volume of the reagent in the multi-reagent pack, volume of liquid transferred using the automatic pipette, temperature of the sample processing platform, type of test performed using the analytical device. Consequently, operational status of the analytical device may include inoperability of one or more components and/or lack of one or more reagents.

In yet another aspect of the inventive subject matter, a method of marketing includes one step in which an analytical device is provided comprising a data transfer interface that receives status data of a component in the analytical device. In another step, the data transfer interface is electronically coupled with a system in a remote location relative to the analytical device, and in yet another step, status data are provided to the remote system using the data transfer interface. In a still further step, the status data are used in the remote system to initiate delivery of a replacement for the component.

Especially contemplated analytical devices analyze binding of an analyte to a substrate on a biochip, and particularly contemplated components include reagents, wherein the status data of the component is the volume of the reagent in the analytical device. Electronic coupling may be performed via modem or other data transfer connection to the Internet, and delivery of the status data may be controlled by a predetermined schedule executed on a processor of the analytical device or by a predetermined schedule executed on a processor of the system in the remote location. Especially preferred initiation of delivery includes automatic generation of a purchase order or inventory control (e.g., packaging and/or labeling of the component, or alert to the customer to indicate status/low supply of the component).

Various objects, features, aspects and advantages of the present invention will become more apparent from the following detailed description of preferred embodiments of the invention, along with the accompanying drawings in which like numerals represent like components.

DETAILED DESCRIPTION

The inventors discovered that one or more analytes can be detected and/or quantified using an integrated analytical device that employs a biochip, wherein (a) processing of the analyte and/or biochip, detection and/or quantification of the analyte is integrated into a process that does not require user intervention, and (b) the integrated analytical device is configured to allow concurrent or subsequent analysis of various biochemically diverse analytes, including nucleic acids, peptides, and small molecules (e.g., enzyme substrates or inhibitors, etc.).

As used herein, the term "analytical device" refers to any device or combination of devices that is employed to detect and/or quantify one or more analytes. Particularly preferred analytical devices include micro array systems, wherein the term "micro array system" refers to an integrated system in which a plurality of analytes are bound to a plurality of substrates on a biochip in predetermined positions, and in which presence and/or quantity of at least one of the analytes is determined.

As also used herein, the term "biochip" generally refers to a carrier upon which a plurality of substrates are immobilized in predetermined positions, and wherein at least one of the substrates binds an analyte from a sample. One class of particularly preferred biochips includes a carrier coupled to a multi-functional matrix layer that is coupled to a substrate, wherein the multi-functional matrix layer provides reduction of at least one of an autofluorescence of the carrier, an incident-light-absorption of the carrier, a charge-effect of the carrier, and a surface unevenness of the carrier, and wherein the substrate binds to an analyte that is disposed in a sample fluid when the sample fluid contacts the biochip.

Alternatively, another class of especially contemplated biochips comprises a plurality of first substrates in a plurality of first predetermined positions, wherein each of the plurality of first substrates belongs to a class selected from the group consisting of a polypeptide, a polynucleotide, a carbohydrate, and a pharmacologically active molecule. A plurality of second substrates in a plurality of second predetermined positions may further be included in such biochips, wherein each of the plurality of second substrates belongs to a class selected from the group consisting of a polypeptide, a polynucleotide, a carbohydrate, and a pharmacologically active molecule, and wherein the class of each of the first substrates and the class of each of the second substrates is not the same. Particularly contemplated biochips are described in co-pending U.S. patent application with the Ser. No. 09/735,402 (filed Dec. 12, 2000) and copending PCT application with the serial number PCT/US01/47991 (filed Dec. 11, 2001), both of which are incorporated by reference herein.

Contemplated biochips may further be disposed in a housing (which may or may not be closed), and particularly preferred biochips comprise a housing at least partially enclosing a multi-substrate chip that includes a reference marker and a plurality of substrates in predetermined positions, wherein the reference marker is illuminated by a first light source at a first angle, and wherein at least one of the plurality of substrates is illuminated by a second light source at a second angle, and wherein the housing is configured such that the first angle and the second angle are not identical. Further particularly contemplated biochips are described in co-pending PCT application with the serial number PCT/US02/03917 (filed Jan. 24, 2002), which is incorporated by reference herein.

As further used herein, the term "analyte" refers to a molecule or assembly of molecules whose presence, quantity, or activity is to be determined from a sample. Particularly contemplated analytes include natural and synthetic nucleic acids, natural and synthetic peptides, pharmacologically active molecules, biological effectors, viruses and portions thereof, bacterial cells and portions thereof, and eukaryotic cells and portions thereof.

For example, where the analyte comprises a natural or synthetic nucleic acid, suitable analytes include oligo- and polynucleotides, DNA and RNA (e.g. cDNA, amplified DNA, in-vitro transcripts, tRNA, rRNA, etc.), nucleic acid analogs (e.g. peptide nucleic acids, phosphorothioate nucleic acids, etc.) and covalent and non-covalent complexes of nucleic acid with functional or non-functional moieties (e.g., radioisotopes, biotin, fluorophor, etc.). Similarly, where the analyte comprises a natural or synthetic peptide, suitable peptides include oligopeptides (e.g., 2-20 amino acids), polypeptides (e.g., 21-20000 amino acids, and higher), linear, cyclic, and/or branched peptides that may include natural and/or non-natural amino acids (in D- or L-configuration), and covalent and non-covalent complexes of peptides with functional or non-functional moieties (e.g. glycoproteins, lipoproteins, biotin, radioisotope labels, etc.).

Contemplated pharmacologically active molecules includes those that interact with reproduction, structural integrity, and/or metabolism of a cell. Consequently, suitable molecules include those interacting with various biological processes including apoptosis, mitosis or meiosis, tubulin assembly and disassembly, enzyme inhibitors or activators, and cis- and trans acting regulatory elements for DNA/RNA expression. Biological effectors particularly include secreted effectors for various organ and systemic functions and include hormones, cytokines, chemokines, and antibodies. With respect to viruses, bacterial and eukaryotic cells it should be recognized that all known viruses, one or more bacterial and eukaryotic cells and fragments thereof (e.g., membranes and their components, ribosomes and their components, various organelles and their components, etc.) are contemplated suitable for use herein. Further contemplated analytes may also include tissue, and especially animal tissue.

In a further especially contemplated aspects, analytes may also be characterized in their ability to (specifically) bind to one or more substrates, wherein the term "binding of the analyte" refers of a non-covalent interaction between the analyte and a substrate to form a complex having a dissociation constant $K_D$ of equal or less than $10^{-4}$M at physiological pH, 20° C., and total salt concentration of less than 150 mM. It should further be appreciated that the term "binding of the analyte" specifically includes binding of a substrate to an enzyme at the active site of the enzyme. Consequently, the term "substrate" as used herein refers to any composition, molecule or assembly of molecules that can bind an analyte to form a complex having a dissociation constant $K_D$ of equal or less than $10^{-4}$M at physiological pH, 20° C., and total salt concentration of less than 150 mM. Particularly preferred substrates include natural and synthetic nucleic acids (e.g., oligonucleotides), natural and synthetic peptides and especially antibodies (and fragments thereof), enzymes, small molecules, viruses or fragments thereof, and one or more bacterial and eukaryotic cells and fragments thereof (e.g., membranes and their components, ribosomes and their components, various organelles and their components, etc.) are contemplated suitable for use herein. Further contemplated substrates may also include tissue, and especially animal tissue.

Thus, the term "non-analyte" refers to any composition, molecule, or assembly of molecules that is not an analyte either by virtue of lack of specific binding and/or by virtue of the chemical composition. For example, where a sample comprises a cytokine and a ribosomal protein, and wherein the substrate comprises an antibody directed against the cytokine, the cytokine will act as the analyte and the ribosomal protein will act as the non-analyte. However, it should be recognized that a sample may also comprise molecules that bind to a substrate with relatively high affinity wherein only one of the molecules is an analyte and the other molecules is not analyte (e.g., single stranded nucleic acid with single base pair mismatch in complementarity relative to a substrate and a single stranded nucleic acid with perfect complementarity relative to the substrate). Here, depending on the test conditions, the analyte may be only one of the analytes or both of the analytes.

Figure 1A:
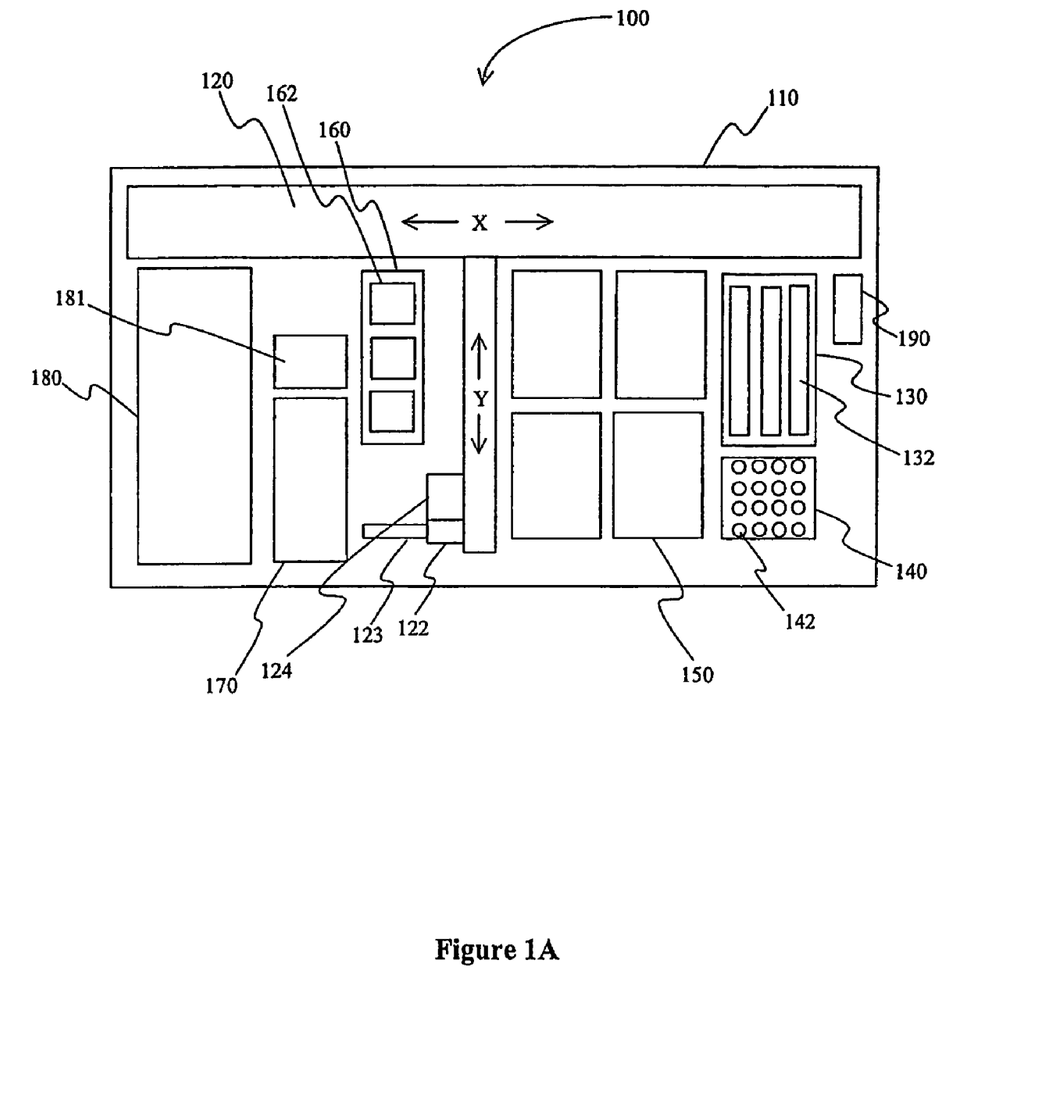
FIG. 1A is a schematic view of an exemplary analytical device according to the inventive subject matter.
Figure 1B:
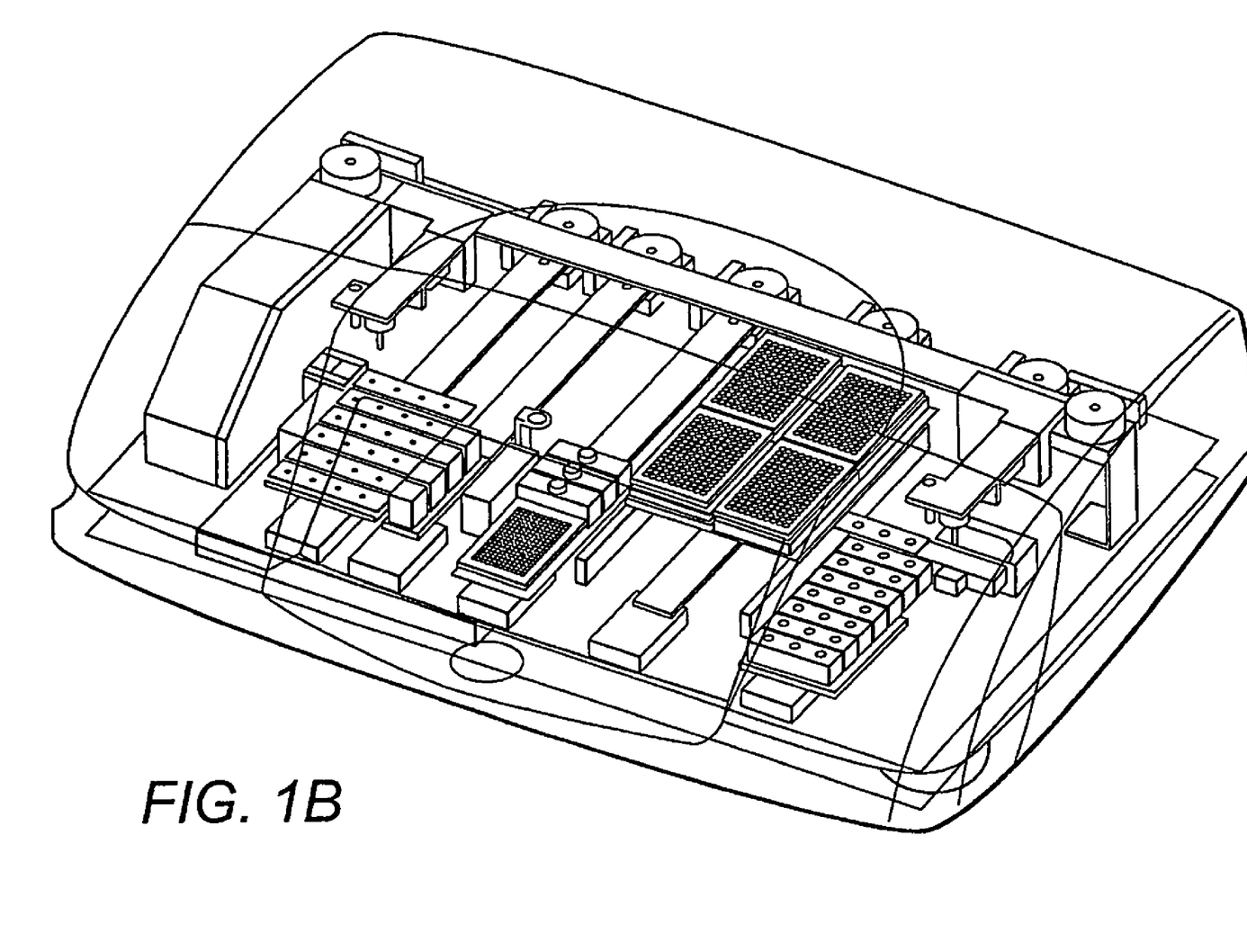
FIG. 1B is a perspective view of an exemplary analytical device according to the inventive subject matter.

FIG. 1A schematically depicts an exemplary integrated micro array system 100 having a housing 110 in which a robotics assembly 120 controls motion of automatic pipette 124 and secondary actuator 122 that controls motion of automatic actuator 123. Fluidics station 130 includes a plurality of multi-reagent packs 132. Sample station 140 preferably comprises a plurality of sample vessels 142 (e.g., a microplate with microwells). Pipette tip storage area 150 includes disposable pipette tips for the automatic pipette 124, and magazine holder 160 includes a plurality of magazines 162 that store at least two, and more typically at least eight biochips. The biochips are moved from the magazine to 162 to a sample processing platform 170 (which may further include an energy source such as an ultrasound source, a microwave source, a heater, and/or a cooler), where the biochip may receive the sample pipetted from the sample vessel 142. Alternatively, a stringency station 181 may be included to achieve higher hybridization specificity (e.g., a thermo element that provides heat and/or cooling to the biochip when position on the stringency station). Subsequent steps of incubation, heating, cooling, adjusting of stringency, and/or washing are then performed on the biochip while the biochip is on the sample processing platform to promote binding of the analyte to the substrate, and to remove non-analytes from the platform. Reagents needed for such sample manipulation steps (including staining reagents for bound analytes) are advantageously retrieved from multi-reagent packs 132. Once the analyte is properly processed on the biochip, the biochip is moved from the platform to the optical detector 180 via automatic actuator 123 for detection and/or quantification of the analyte. A data transfer device 190 is electronically coupled to various components of the analytical device and provides data to a remote system or person other than the operator (not shown). A perspective view of an exemplary analytical device is depicted in FIG. 1B.

Figure 2:
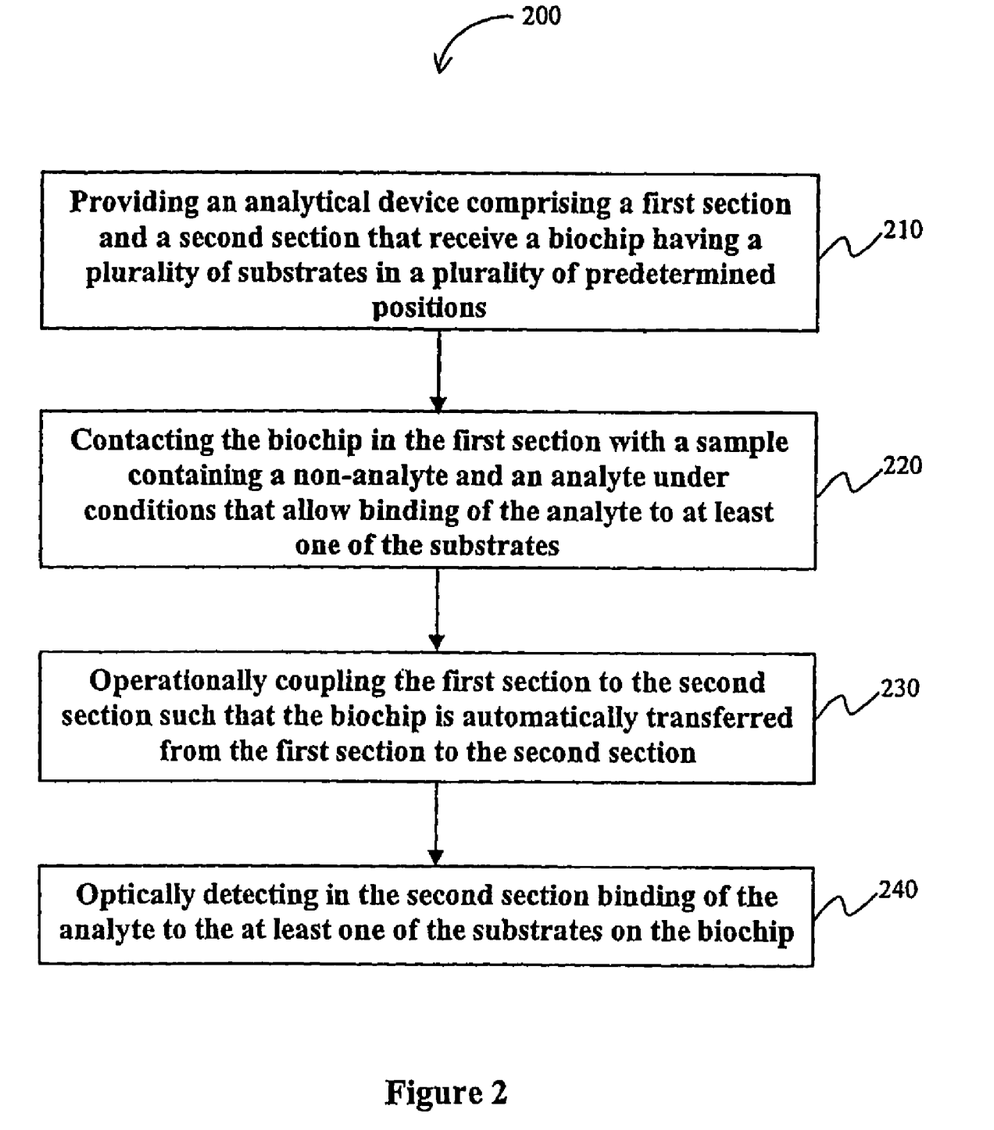
FIG. 2 is a flow chart of a method of analyzing an analyte on a biochip according to the inventive subject matter.

Thus, in one particularly preferred aspect of the inventive subject matter, a method of analyzing an analyte on a biochip will include a step in which an analytical device is provided that has a first section and a second section, and wherein both sections receive a biochip having a plurality of substrates in a plurality of predetermined positions. In another step, the biochip is contacted in the first section with a sample containing a non-analyte and an analyte under conditions that allow binding of the analyte to at least one of the substrates. In yet another step, the first section is operationally coupled to the second section such that the biochip is automatically transferred from the first section to the second section, and in still another step, binding of the analyte to the at least one of the substrates on the biochip is optically detected in the second section.

Particularly contemplated analytical devices include those in which detection and at least one of (a) sample application to the biochip, (b) binding of an analyte to a substrate on the biochip, (c) adjusting the hybridization stringency (e.g. via change in temperature of the analyte substrate complex, or change in ionic strength in the environment of the analyte substrate complex, or change in solvent), and (d) washing the biochip such that the analyte remains bound and at least 75% (more typically at least 95%, and most typically at least 99%) of the non-analyte is washed off the biochip are performed within the same device, preferably without user intervention (i.e., without a user manually manipulating the biochip). Further especially contemplated analytical devices include integrated micro array systems that may further comprise at least one of a sample processing platform, one or more multi-reagent packs, a robotics assembly, and an optical or other detector.

With respect to the first section it is contemplated that such sections may have various configurations so long as such first sections are configured to receive a biochip, wherein the biochip can be contacted with a sample containing a non-analyte and an analyte under conditions that allow binding of the analyte to at least one of the substrates on the biochip. Consequently, particularly suitable first sections will include a generally flat surface that engages with the biochip, or may include at least one guide element (e.g., a rail, a protrusion, or other element) that engages with the biochip to receive and retain the biochip in a predetermined position. For example, appropriate first sections may be shaped in form of a generally flat platform, a U-shaped tray that receives the biochip. Furthermore, it should be appreciated that contemplated first sections may be configured such that they receive at least a second biochip, and in especially preferred aspects, suitable first sections will be configured to receive typically between one and 10 biochips.

Particularly preferred first sections may be configured to provide preselected conditions that allow binding of the analyte to at least one of the substrates. For example, suitable first sections may be coupled to an energy source that provides energy to the biochip (and thus to the substrate-analyte complex) directly or indirectly. Where direct energy transfer is desired, the energy source may include thermal radiation/convection and/or electromagnetic radiation (e.g., a microwave source) to deliver the energy to the substrate-analyte complex on the biochip. Alternatively, direct energy sources may also include ultrasound probes that contact a fluid in the biochip, wherein the fluid includes the substrate-analyte complex.

On the other hand, where indirect energy transfer is desired, suitable energy sources include thermal elements (e.g., Peltier element, heater, or cooler) or other heater and/or cooler elements that provide heat or cooling to the substrate-analyte complex on the biochip through the first section. For example, suitable first sections may be fabricated from aluminum and may include a Peltier element coupled on one side, while the biochip will be disposed on the opposite side.

In still further especially preferred aspects, the biochip is provided to the first section from a magazine using an automatic actuator that moves the biochip from the magazine along at least one coordinate to the first section (the magazine is preferably disposed within the analytical device). For example, a magazine may be positioned proximal to the first section and include two openings, wherein the actuator is directed into the first opening and the biochip proceeds through the second opening onto the first section (e.g. sample processing platform). However, in alternative aspects, the biochip may also be provided to the first section manually by the user or automatically via any appropriate feeding mechanism. For example, contemplated feeding mechanisms include chutes, conveyor belts, etc. Moreover, it should be recognized that the first section may be moved relative to the second section (or other component in the analytical device), and it is especially preferred that the first section is movable along at least one coordinate in the analytical device (e.g., on a rail moved by a stepper motor)

With respect to the second section, it is generally preferred that the second section will receive the biochip (preferably directly from the first section) and further comprises an optical detector that detects binding of the analyte to the substrate on the biochip. Thus, suitable second sections will be located within the analytical device in a position proximal to the first section and are preferably configured such that the biochip can be directly and automatically moved from the first to the second section (e.g. include a generally horizontal surface, guide rail or other element that engages with the biochip to receive and retain the biochip).

For example, direct and automatic movement (i.e., movement without the user manually moving the biochip) of the biochip may include horizontally moving the biochip from an adjacent first platform to the second platform using an automatic actuator or a conveyor belt-type mechanism. On the other hand, direct and automatic movement of the biochip may also include sliding the biochip from a level that is higher than the second section to the second section (e.g., by tilting the first section). Alternatively, movement of the biochip may also include direct and automatic transfer of the biochip from the first section to the second section using a robotic assembly that controls movement of the biochip along two, and more typically three coordinates.

Furthermore, it is contemplated that suitable second sections may be in a fixed or movable position within the analytical device, and where the second section is movable, it is contemplated that movement of the second section may be along one, two, or three coordinates. Moreover, it is contemplated that in preferred aspects of integrated micro array systems at least one environmental parameter in the second section may be controlled. For example, in particularly contemplated configurations of second sections, temperature and humidity may be controlled (e.g., via Peltier element and/or humidifier).

Contemplated optical detectors generally include all optical devices that can detect an optical signal in a predetermined position on the biochip, and especially contemplated detectors include a photomultiplier tube, a charge coupled device (CCD), which may be optically coupled to a confocal, and/or dark field microscope. Contemplated optical signals detected by such optical detectors include a fluorescence signal, a chemiluminescence signal, and/or a phosphorescence signal. There are numerous optical detectors known in the art to detect optical signals from biochips, and all of the known devices are considered suitable for use herein. In further preferred configurations, the biochip includes a reference marker that produces a reference signal upon illumination, and the optical detector is focused using a reference signal (infra).

Therefore, depending on the particular configuration of first and second sections, it should be appreciated that there are numerous configurations of operational coupling the first section to the second section. However, it is generally contemplated that all modes of operational coupling will allow automatic transfer of the biochip from the first to the second section. The term "automatic transfer" of the biochip as used herein means that the biochip is moved from the first to the second section without a user manually contacting and/or moving the biochip. Consequently, operational coupling may be achieved by positioning the first and second sections relative to each other such that a biochip may be automatically transferred (e.g., via robotic assembly, conveyor belt, or actuator that moves in one or more directions) from the first to the second section, wherein contemplated positioning may include a fixed position of one section relative to the other section (e.g., first and second sections are in a fixed and abutting position), or a movable positioning where one section moves relative to the other section (e.g., first section moves along a guide rail actuated by a motor into abutting position with the second section).

Suitable analytical devices may further include various sensors that provide a computer (electronically coupled to the analytical device and controlling at least some of the functions [e.g., length and temperature of incubation steps, type of assay performed, data analysis, etc.] of the analytic device) with environmental information, and especially preferred sensors include a humidity sensor and/or a temperature sensor. Yet further contemplated sensors may include barcode readers, and it is especially preferred that the barcode reader (s) will read barcodes on at least one of the reagent pack, the biochip, and the sample container.

With respect to contemplated biochips, it is generally contemplated that suitable biochips will include a carrier to which a plurality of substrates in predetermined positions are coupled, wherein at least one of the substrates is capable of selectively binding an analyte. One class of particularly preferred biochips includes a carrier coupled to a multi-functional matrix layer that is coupled to a substrate, wherein the multi-functional matrix layer provides reduction of at least one of an autofluorescence of the carrier, an incident-light-absorption of the carrier, a charge-effect of the carrier, and a surface unevenness of the carrier, and wherein the substrate binds to an analyte that is disposed in a sample fluid when the sample fluid contacts the biochip.

Alternatively, another class of especially contemplated biochips comprises a plurality of first substrates in a plurality of first predetermined positions, wherein each of the plurality of first substrates belongs to a class selected from the group consisting of a polypeptide, a polynucleotide, a carbohydrate, and a pharmacologically active molecule. A plurality of second substrates in a plurality of second predetermined positions may further be included in such biochips, wherein each of the plurality of second substrates belongs to a class selected from the group consisting of a polypeptide, a polynucleotide, a carbohydrate, and a pharmacologically active molecule, and wherein the class of each of the first substrates and the class of each of the second substrates is not the same. In especially contemplated aspects, at least one of the plurality of substrates is non-covalently coupled to the biochip via a crosslinker. Particularly contemplated biochips are described in co-pending U.S. patent application with the Ser. No. 09/735,402 and copending PCT application with the serial number PCT/US02/47991 (supra).

Contemplated biochips may further be disposed in a housing (which may or may not be closed), and particularly preferred biochips comprise a housing at least partially enclosing a multi-substrate chip that includes a reference marker and a plurality of substrates in predetermined positions, wherein the reference marker is illuminated by a first light source at a first angle, and wherein at least one of the plurality of substrates is illuminated by a second light source at a second angle, and wherein the housing is configured such that the first angle and the second angle are not identical. Further particularly contemplated biochips are described in co-pending PCT application with the serial number PCT/US02/03917 (supra).

In especially preferred aspects of contemplated methods, a second biochip with a plurality of second substrates in a plurality of predetermined positions may be provided to at least one of the first and second sections, and the second biochip is contacted in the first section with a sample containing a second non-analyte and a second analyte under conditions that allow binding of the second analyte to at least one of the second substrates of the second biochip. While not limiting to the inventive subject matter, it is contemplated that the substrates of the first biochip and the second biochip belong to different classes. For example, while the first biochip may include nucleic acids as substrates, the second biochip may include peptides as a substrate. Of course, it should also be recognized that contemplated biochips may also include at least two different types of substrates, wherein contemplated types of substrates include nucleic acids, peptides, small molecules, pharmaceutically active molecules, a virus, bacterial or eukaryotic cell or fragments thereof, and tissues. Consequently, particularly preferred samples include biological fluids (e.g., whole or processed blood, plasma, serum, biopsy specimens, urine, spinal fluid, saliva, etc.), wherein particularly preferred analytes include tissues, nucleic acids, peptides, and enzyme inhibitors.

Depending on the particular type of sample and/or substrate on the biochip, it is generally contemplated that the step of contacting the biochip with the sample includes an automatic application, however, manual application of the sample to the biochip is also considered suitable. In a particularly preferred aspect, the sample is a liquid and is pipetted with an automatic pipette (i.e., aspiration of the fluid is performed using a motor or electric vacuum pump) that is disposed within the analytical device. There are numerous automatic pipettes known in the art and all of the known automatic pipettes are considered suitable for use herein. Especially preferred automatic pipettes are Gilson, Eppendorf, and Rainin automatic pipettors, which may or may not be further modified.

Particularly preferred modifications of contemplated automatic pipettes will include at least one of a volume sensor and a tip height sensor. For example, one particularly preferred volume sensor may employ a laser beam within the pipette tip, wherein the laser beam is employed to determine the height (and with this the volume) of the aspirated liquid within the tip. Another especially preferred aspect includes an ultrasound (or second laser) beam that is employed to determine the distance between the fluid dispensing end of the pipette tip and a surface to which the fluid is to be dispensed.

With respect to the step optically detecting binding of the analyte, it is generally contemplated that all known detection methods are suitable for use herein. However, in particularly preferred detection steps, non-analytes are removed from the biochip prior to detection by providing conditions that promote dissociation or non-binding of the non-analyte. For example, suitable conditions may include washing with wash fluids (e.g., provided by a multi-reagent pack), a temperature change (e.g., heating), sonication, etc. Optical detection of binding may be performed using detection of radiation, luminescence, or light absorption of a dye or other marker that is coupled to the analyte (wherein the step of coupling the dye or other marker may be performed in a separate step).

Particularly preferred detections include detection of chemiluminescence, fluorescence, and/or phosphorescence, which may be performed using a photomultiplier in conjunction with a dark field microscope or confocal microscope (which may be located in a separate section or the section). Especially preferred optical detection includes a step in which the focal plane is determined in a process that avoids illumination (and therefore photo-bleaching) of the analyte that is bound to the substrate.

Figure 3:
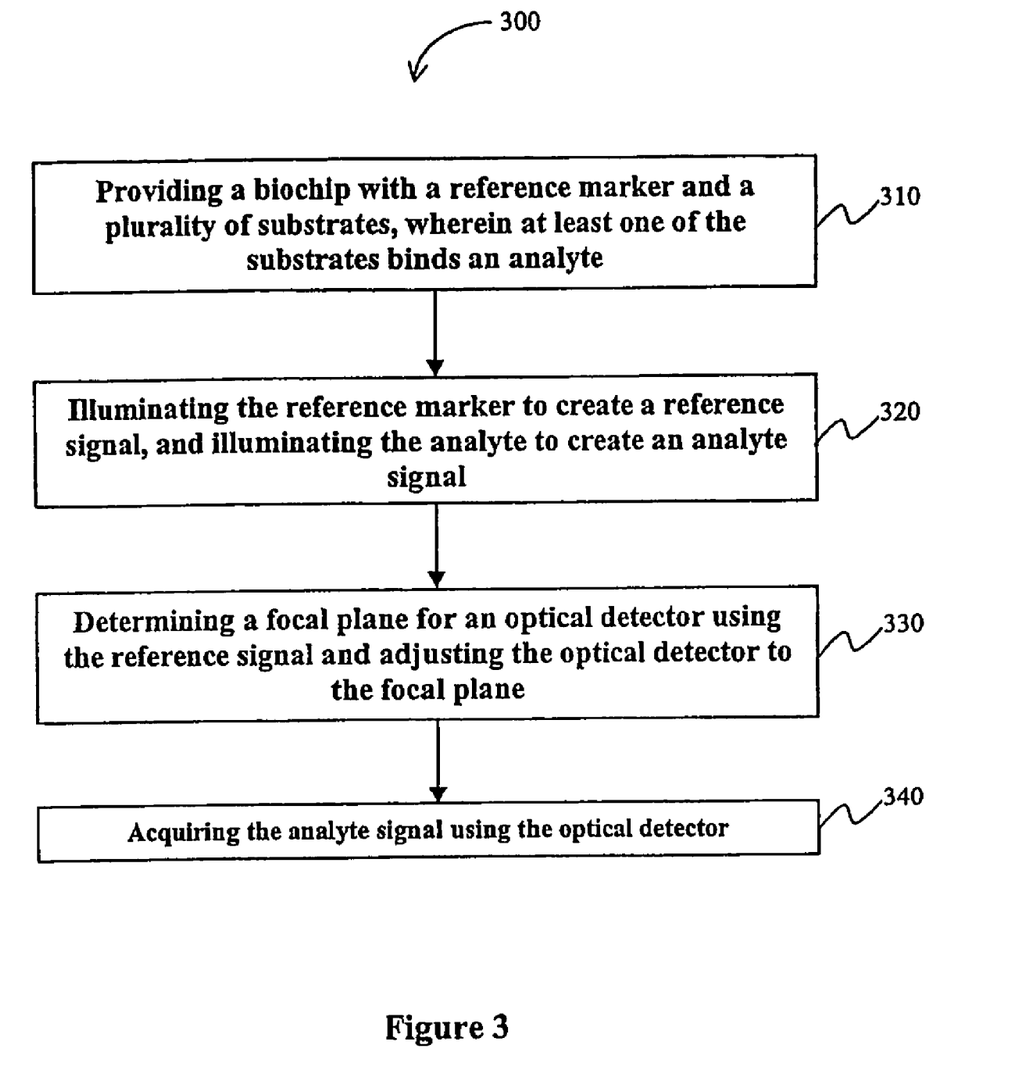
FIG. 3 is a flow chart of another method of analyzing an analyte on a biochip according to the inventive subject matter.

Thus, in another especially preferred aspect of the inventive subject matter, a method of analyzing an analyte on a biochip may include providing a biochip with a reference marker and a plurality of substrates, wherein at least one of the substrates binds an analyte, illuminating the reference marker to create a reference signal, and illuminating the analyte to create an analyte signal, determining a focal plane for an optical detector using the reference signal and adjusting the optical detector to the focal plane, and acquiring the analyte signal using the optical detector.

With respect to the biochip, the same considerations as discussed above apply. Particularly contemplated biochips will include at least one, more preferably two, and most preferably four reference markers (which may be positioned at the corners of the biochip), wherein suitable reference markers include numerous optically detectable elements. Among other elements, suitable reference markers include fluorophors, luminogenic substrates, and phosphorescent compounds. Alternatively, dye of dye mixtures may also be suitable.

Furthermore, appropriate biochips may have one or more classes of substrates (which may or may not be chemically distinct), and contemplated substrates include nucleic acids, peptides, and enzyme inhibitors, wherein at least one of the substrates is non-covalently coupled to the biochip via a crosslinker. Especially preferred crosslinkers include known affinity pairs, which may comprise peptides or small molecules. For example, contemplated crosslinkers are biotin/streptavidin, antibody (fragment)/hapten, chelated nickel/polyHistidyl moiety, etc., wherein either of the affinity pair may be (covalently or non-covalently) coupled to the biochip. Consequently, binding of the analyte to the substrate is preferably non-covalent binding, however, covalent binding is not excluded.

In further preferred aspects, the biochip is moved within the analytical device from a sample processing platform (e.g., the first section, supra) to a detector (e.g., in the second section, supra) using an automatic actuator. Contemplated automatic actuators include robotic actuators that are controlled in at least two, and more preferably three dimensions via step motors. However, other means of moving are also contemplated suitable and include conveyor belts, slides, etc.

Contemplated steps of illuminating the reference marker may be performed in numerous manners so long as the reference marker receives sufficient light to enable optical detection and focusing. Thus, suitable illumination of the reference marker includes dark field illumination (e.g., through the housing of the biochip), which is particularly preferably where the analyte comprises a light-sensitive marker. However, direct illumination of the reference marker is also contemplated suitable for use herein. Consequently, the light sources for illumination may vary considerably and may include illumination of the reference marker with a light source other than the light source employed for illumination of the analyte. Exemplary light sources include various laser and laser diodes, LED diodes, incandescent an dfluorescent light sources, etc.

Therefore, the reference marker may be employed to determine the focal plane of the detection device (preferably confocal microscope) by illuminating the reference marker which is in known spatial relationship to the position of the analyte. Consequently, and especially where more than one reference marker is employed, correct focusing of analytes disposed on an uneven surface of the biochip is possible without an otherwise required step of refocusing to each new analyte. Furthermore, the use of an independent reference marker will advantageously allow illumination of the biochip (for focusing purposes) with light at a wavelength that will provide significantly reduced photo-damage to the analyte, or even no photo-damage at all. Adjustment of the optical detector may be performed in various manners and will typically include a relative movement between the optical detector and the biochip in at least one dimension. However, it is generally preferred that the biochip is moved within the detection unit on a platform that can be moved in at least one dimension, and more typically on a platform that can be moved in all three dimensions.

Thus, the analyte signal (which may be directly generated by the analyte or indirectly by a marker coupled to the analyte) includes signals selected from the group consisting of a fluorescence signal, a chemiluminescence signal, and a phosphorescence signal. The particular nature of the signal will typically be determined at least in part by the particular analyte, and a person of ordinary skill in the art will readily determine the appropriate signal source.

Figure 4:
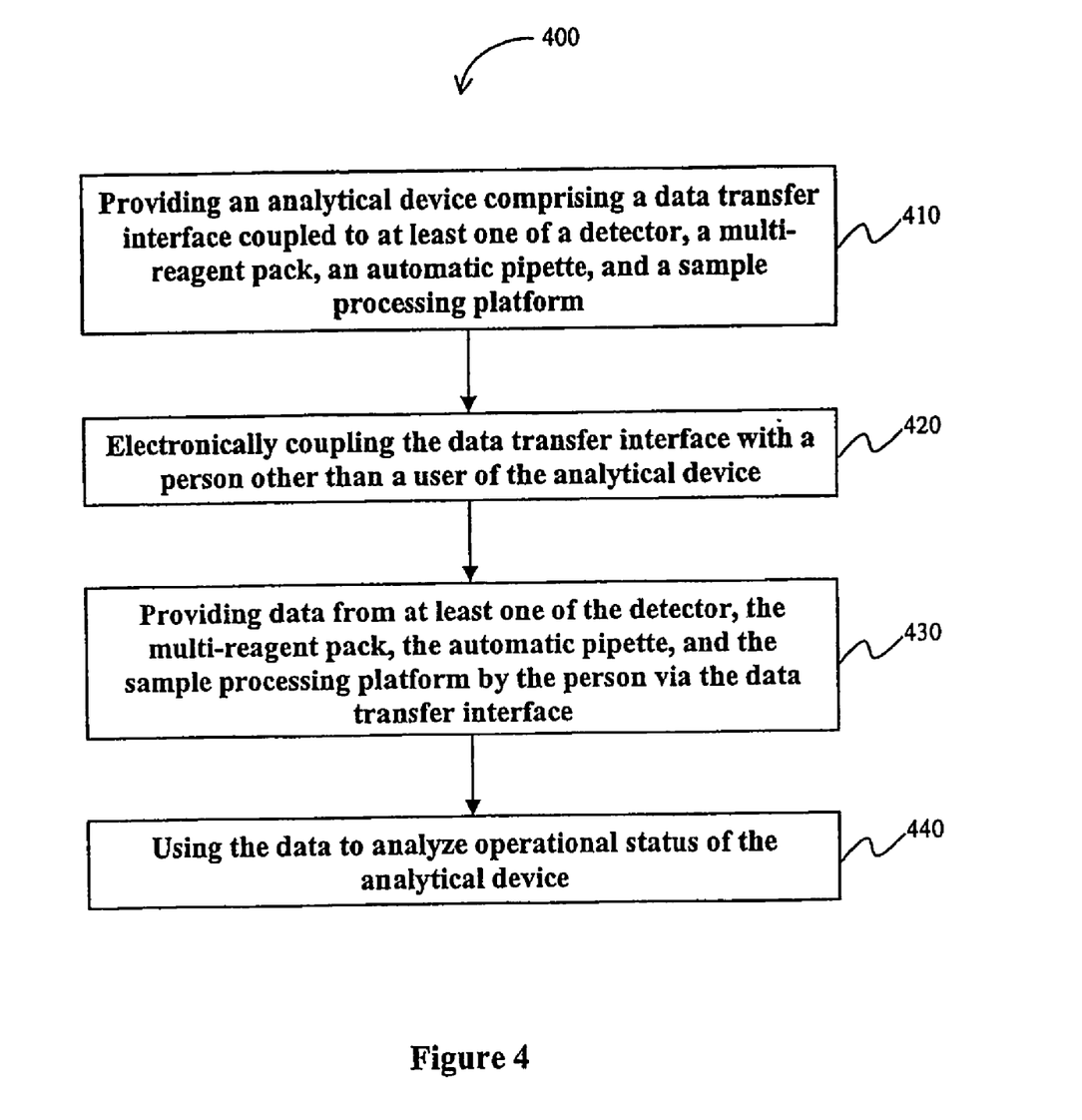
FIG. 4 is a flow chart of a method of operating an analytical device according to the inventive subject matter.

In a still further especially contemplated aspect of the inventive subject matter, and particularly where the analytical device includes a data transfer interface, the inventors contemplate a method of operating an analytical device that includes a step of providing an analytical device comprising a data transfer interface coupled to at least one of a detector, a multi-reagent pack, an automatic pipette, and a sample processing platform, electronically coupling the data transfer interface with a person other than a user of the analytical device, providing data from at least one of the detector, the multi-reagent pack, the automatic pipette, and the sample processing platform to the person via the data transfer interface, and using the data to analyze operational status of the analytical device.

Especially suitable data transfer interfaces include electronic data transfer interfaces used in personal computers such as telephone or cable modems. Consequently, suitable data transfer interfaces are preferably controlled by a microprocessor (most preferably the microprocessor that controls operation of the analytic device) within the analytical device. In a particularly contemplated mode of operation, the data transfer interface is temporarily electronically connected to a remote computer via a telephone modem, wherein either the analytical device or the remote compute initiates electronic communication.

In particularly contemplated aspects, the data transfer interface is electronically coupled to the detector, a multi-reagent pack, the automatic pipette, and/or the sample processing platform, wherein the data transfer interface receives or provides data from the detector, multi-reagent pack, automatic pipette, and/or sample processing platform. For example, the detector may provide data relating to signal strength, wavelength, calibration signals, or type of assay to the interface, while the multi-reagent pack may provide data regarding the (remaining) contents of the reagents in the pack, the type of test performed, the date the pack was purchased and/or first used, etc. Similarly, the automatic pipette may provide data relating to number of pipetting functions, size of tips employed, etc. Thus, the data transfer interface may collect and/or disseminate data that are relevant for the operational status of the analytical device. Consequently, it should be appreciated that the data transfer interface is a bi-directional data transfer interface, that is, data are provided to and from the analytical device.

Consequently, in one aspect of the inventive subject matter, the data transfer interface may be electronically coupled to a person other than the user of the analytical device to provide data from the detector, multi-reagent pack, automatic pipette, sample processing platform, or other component (hard drive, CPU, pipette rack, etc.). Such configurations may be especially advantageous where an analytical device has become inoperable or provide a user with an error notification. The user may then activate electronic communication (manually or by default) between the data transfer interface and a computer in a remote location, wherein a person other than the user (e.g., service technician) request or receives the status data to provide immediate diagnosis of the analytical device from a remote location. The term "person other than the user" as used herein refers to a person does not initiate, continue, or terminate (including analysis of test results) a test using the analytical device, typically while proximal to the analytical device. The term "proximal to the analytical device" as used herein means within the same room, or associated with the data generated by the analytical device (e.g., a physicians office). Thus especially contemplated persons other than a user include sales staff for components or reagents of the analytical device, service technicians of the analytical device, etc.

With respect to the step of providing the data, it should be recognized that all known methods of data transfer are contemplated, particularly including the person other than the user remotely requesting data, and the user initiating electronic communication between the analytical device and the person other than the user. Thus, the step of providing may preferably be executed via an Internet or via a modem connection and may be performed in response to an action of the user of the analytical device.

Particularly contemplated data include type of reagent in the multi-reagent pack, volume of at least one reagent in the multi-reagent pack, volume of liquid transferred using the automatic pipette, temperature of the sample processing platform, type of test performed using the analytical device, batch number of reagent in the multi-reagent pack, date manufactured of reagent in the multi-reagent pack, and expiration date of reagent in the multi-reagent pack. Consequently, the operational status will include inoperability (e.g., inoperable due to lack of reagent, inoperable due to failure of the automatic pipette, inoperable due to incompatibility of reagent with a selected test, and/or inoperable due to failure of the detector) of the analytical device, current activity of the analytical device (e.g., pipetting, focusing, detecting, etc.), and supply status (e.g., how many test reagents left).

Figure 5:
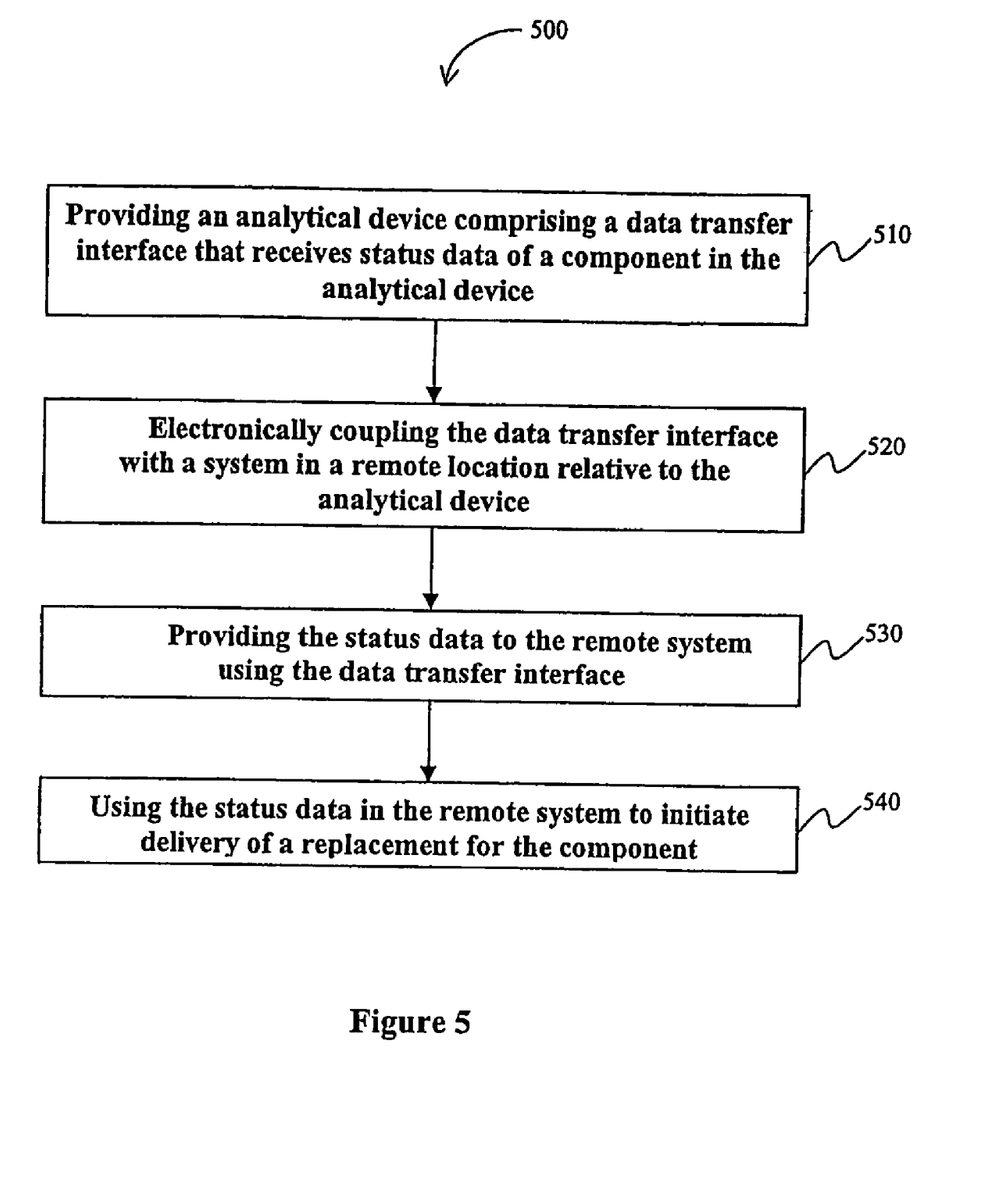
FIG. 5 is a flow chart of a method of marketing according to the inventive subject matter.

Therefore, a further particularly contemplated aspect of the inventive subject matter includes a method of marketing in which an analytical device is provided, wherein the device comprises a data transfer interface that receives status data of a component in the analytical device. The data transfer device is then electronically coupled to a system in a remote location relative to the analytical device, and the data transfer device provides then the status data to the remote system using the data transfer interface, wherein the status data are used in the remote system (or analytical device) to initiate delivery of a replacement for the component.

With respect to the analytical device, the data transfer interface, status data, the component, the same considerations as discussed above apply. Particularly preferred analytical devices include those that analyze binding of an analyte to a substrate on a biochip. However, numerous other analytical devices are also considered suitable and include analytical and/or preparative systems (e.g., HPLC, GC, etc.). Further especially preferred components include reagents (solid, liquid, or gaseous), wherein the status data of the component is (remaining) volume of the reagent in the analytical device. However, non-reagent components, and especially disposable non-reagent components are also contemplated. Thus suitable components include pipette tips, wherein the status data of the component is the number of remaining pipette tips in the analytical device It should further be recognized that the step of electronically coupling may include a permanent coupling or a temporary coupling (e.g., user, or device initiated). However, especially suitable couplings include coupling the analytical device with an Internet. In further contemplated aspects, the step of providing the status data is controlled by a predetermined schedule executed on a processor of the analytical device. Alternatively, the step of providing the status data may be controlled by a predetermined schedule executed on a processor of the system in the remote location.

It is generally contemplated that the status data may be used in the remote system (or in the analytical device) to initiate delivery of a replacement for the component. The term "initiate delivery" as used herein refer to an event leading to a decision whether or not to provide a customer with a product. Thus, initiation of delivery may include automatic generation of a purchase order, automated offer to purchase from the remote system to the analytical device, etc. Consequently, contemplated methods and configurations may be employed for inventory control and management on the side of the operator of the analytical device.

Therefore, contemplated systems will provide an operator with the capability to quantitatively and qualitatively analyze one or more analytes in one or more samples with minimum manual intervention. For example, while numerous known systems separate sample and/or analyte handling (e.g., application, washing, hybridization) from analyte detection, the contemplated system will in one preferred aspect perform sample and/or analyte handling and analyte detection in an automated and typically continuous manner.

Thus, contemplated systems will include the following subsections: Sample and reagent handling, disposable handling, microarray processing, stringency station, optical detection system, waste handling, and data/result analysis. These sections handle all the processing required for DNA and Proteomic analysis for the following not exclusive list: SNP and STR analysis, microsatellite analysis, gene- and protein expression analysis, and protein quantification and identification.

Consequently, one or more of the following processing steps may be included in contemplated analytic systems: Sample and reagent dispensing operations, analysis of environmental conditions for sample and reagent, wash processes using aspiration dispenser, ultrasonic energy and heat, use of ultrasonic energy for mixing to improve hybridization and binding, bar code for reagent tracking and sample identification, sonic irradiation for chip surface detection, laser irradiation for volume and surface detection, and the use of a reagent module as a communication link between at least two of manufacturing, assay development scientist, user and technical support without any intervention from the operator. In further contemplated aspects, stringency is preferably controlled at least in part determined by heat (e.g., thermal stringency for improving specificity), and optical detection employs a two wavelength system for excitation and detection using confocal microscope technology. Assay development software is contemplated to assist in automation of new tests.

In yet further contemplated aspects, the software/operator interface will provide the system with specific test requirement for a specific sample, which may be downloaded from a host computer. Furthermore, it is contemplated that the interface may also be used to transmit results through web or modem. Thus, a contemplated operation communication link may include an integrated color monitor, a mouse and keyboard, a R/W CD, 40 GB of hard drive, and bioinformatics software for data/result analysis.

Thus, specific embodiments and applications of integrated micro array systems have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of analyzing an analyte on a biochip, comprising:

providing an analytical device that comprises within a housing a first section and a second section that receive a biochip having a plurality of substrates in a plurality of predetermined positions;

using a robotics assembly that comprises a first portion that is configured to allow movement of a second portion with respect to a x-coordinate, wherein the second portion comprises an automated pipette and a second actuator, wherein the second portion is configured to allow movement of the automated pipette and second actuator with respect to a y-coordinate;

using the automated pipette to contact the biochip in the first section with a sample containing a non-analyte and an analyte under conditions that allow binding of the analyte to at least one of the substrates;

moving the biochip in a horizontal motion along a horizontal surface from the first section to the second section using the second actuator;

calculating a focal plane using a plurality of reference signals obtained from a plurality of reference markers disposed on the biochip such that a correct focus is calculated for each of the analytes without a step of refocusing each of the analytes where the analytes are disposed on an uneven surface of the biochip;

optically detecting with an optical device in the second section binding of the analyte to the at least one of the substrates on the biochip;

wherein a position of the plurality of the analytes is computed using a predetermined relationship of the plurality of reference markers to the plurality of analytes; and wherein the reference markers are illuminated by a first light source at a first angle, and wherein at least one of the plurality of substrates is illuminated by a second light source at a second angle, and wherein the first angle and the second angle are not identical.

2. The method of claim 1 wherein the biochip is provided to the first section from a magazine using the second actuator, and wherein the magazine is disposed within the analytical device.

3. The method of claim 1 wherein the first section is configured to receive at least a second biochip.

4. The method of claim 1 wherein the first section further comprises an energy source.

5. The method of claim 4 wherein the energy source is selected from the group consisting of an ultrasound source, a microwave source, a heater, and a cooler.

6. The method of claim 1 wherein the sample comprises a biological fluid, and wherein the analyte is selected from the group consisting of a tissue, a nucleic acid, a peptide, and an enzyme inhibitor.

7. The method of claim 1 wherein the plurality of substrates comprise at least one of a nucleic acid, a peptide, and an enzyme inhibitor, and wherein at least one of the plurality of substrates is non-covalently coupled to the biochip via a crosslinker.

8. The method of claim 1 wherein the step of contacting includes heating the biochip within the analytical device.

9. The method of claim 1 wherein the optical device comprises a confocal microscope or a dark field microscope.

10. The method of claim 1 wherein the step of optically detecting comprises detecting a signal selected from the group consisting of a fluorescence signal, a chemiluminescence signal, and a phosphorescence signal.

11. The method of claim 1 further comprising:
providing a second biochip having a plurality of second substrates in a plurality of predetermined positions;
contacting the second bio chip in the first section with a sample containing a second non-analyte and a second analyte under conditions that allow binding of the second analyte to at least one of the second substrates of the second biochip;
wherein the plurality of substrates comprises a nucleic acid, and wherein the plurality of second substrates comprises a peptide.

12. A method of analyzing an analyte on a biochip, the method comprising:
providing a biochip that is at least partially enclosed by a housing, wherein the biochip comprises a plurality of reference markers and a plurality of substrates, wherein a first and a second substrate are capable of binding a first and a second analyte, respectively;
illuminating the plurality of reference markers to create a plurality of reference signals, and illuminating the first and second analytes to create first and second analyte signals;
determining a focal plane using the plurality of reference signals and adjusting the optical detector to the focal plane of each of the first and second analytes;
wherein the focal plane is determined such that a correct focus is calculated for each of the analytes without a step of refocusing each of the analytes where the analytes are disposed on an uneven surface of the biochip;
wherein the reference marker is illuminated by a first light source at a first angle, and wherein at least one of the plurality of substrates is illuminated by a second light source at a second angle, and wherein the first angle and the second angle are not identical; and
acquiring first and second analyte signals using the optical detector at the respective correct focus for the first and second analytes.

13. The method of claim 12 wherein the plurality of reference markers comprises a compound selected from the group consisting of a fluorophor, a luminogenic substrate, or a phosphorescent compound.

14. The method of claim 12 wherein at least one of the first and second substrates is selected from the group consisting of a nucleic acid, a peptide, and an enzyme inhibitor, and wherein the at least one of the substrates is non-covalently coupled to the biochip via a crosslinker.

15. The method of claim 12 wherein the binding of the first and second analytes to at least one of the first and second substrates is non-covalent binding.

16. The method of claim 12 wherein the step of providing the biochip comprises pushing in a horizontal movement the biochip from a sample processing platform to a detector using an automatic second actuator that is coupled to a robotics assembly.

17. The method of claim 12 wherein the step of illuminating the plurality of reference markers comprises illumination in a dark field.

18. The method of claim 12 wherein the step of illuminating the first and second analyte comprises illumination with a laser.

19. The method of claim 12 wherein illuminating the plurality of reference markers and illuminating the first and second analytes are performed using independent light sources.

20. The method of claim 12 wherein the optical detector comprises a confocal microscope.

21. The method of claim 12 wherein the first and second analyte signals are a signal selected from the group consisting of a fluorescence signal, a chemiluminescence signal, and a phosphorescence signal.

* * * * *